United States Patent
Downey

(10) Patent No.: US 8,656,992 B2
(45) Date of Patent: *Feb. 25, 2014

(54) STIMULATION OF BIOGENIC GAS GENERATION IN DEPOSITS OF CARBONACEOUS MATERIAL

(71) Applicant: Ciris Energy, Inc., Centennial, CO (US)

(72) Inventor: Robert Downey, Centennial, CO (US)

(73) Assignee: Ciris Energy, Inc., Centennial, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/913,731

(22) Filed: Jun. 10, 2013

(65) Prior Publication Data

US 2013/0264052 A1    Oct. 10, 2013

Related U.S. Application Data

(63) Continuation of application No. 12/455,431, filed on Jun. 2, 2009, now Pat. No. 8,459,349.

(60) Provisional application No. 61/130,796, filed on Jun. 3, 2008.

(51) Int. Cl.
*E21B 43/22*     (2006.01)
*E21B 43/16*     (2006.01)

(52) U.S. Cl.
USPC .......................................... 166/246; 305/300

(58) Field of Classification Search
USPC ....................................... 166/246, 305.1, 300
See application file for complete search history.

(56) References Cited

U.S. PATENT DOCUMENTS

| 7,640,978 B2 | 1/2010 | Pfeiffer et al. |
| 7,696,132 B2 | 4/2010 | Pfeiffer et al. |
| 8,459,349 B2 * | 6/2013 | Downey ........................ 166/246 |
| 2006/0223160 A1 | 10/2006 | Vanzin |
| 2006/0254765 A1 | 11/2006 | Pfeiffer et al. |
| 2007/0261843 A1 | 11/2007 | Pfeiffer et al. |
| 2009/0193712 A1 | 8/2009 | Verkade et al. |

* cited by examiner

*Primary Examiner* — Zakiya W Bates
*Assistant Examiner* — Silvana Runyan
(74) *Attorney, Agent, or Firm* — Elliot M. Olstein; Raymond J. Lillie

(57) ABSTRACT

The invention relates to treating of subterranean formations to increase the susceptibility (by way of chemical break down or solubilization, but not necessarily limited by these or any other theories) of large carbonaceous molecules therein, such as comprise coal, to bioconversion into methane and other useful hydrocarbon products by indigenous and/or non-indigenous microbial consortia, by introducing into the subterranean formations: (a) a solution containing at least one of an oxoacid ester of phosphorus or a thioacid ester of phosphorus; and (b) one or more other chemical compounds/chemical entities selected from the group consisting of: hydrogen, carboxylic acids, esters of carboxylic acids, salts of carboxylic acids, oxoacids of phosphorus, salts of oxoacids of phosphorus, vitamins, minerals, mineral salts, metals, and yeast extracts. In an additional embodiment the treating of the subterranean formation further comprises introducing into the subterranean formation a microbial consortia (preferably comprised of methanogens).

13 Claims, 3 Drawing Sheets

_(US 8,656,992 B2)_

STIMULATION OF BIOGENIC GAS GENERATION IN DEPOSITS OF CARBONACEOUS MATERIAL

This application is a continuation of application Ser. No. 12/455,431, filed Jun. 2, 2009, which claims priority based on provisional Application Ser. No. 61/130,796, filed Jun. 3, 2008, the contents of which are incorporated herein by reference in their entireties.

The present invention relates to the production of methane, carbon dioxide, gaseous and liquid hydrocarbons, and other valuable products from subterranean formations, in-situ, utilizing indigenous and/or non-indigenous microbial consortia that are capable of methanogenesis.

Methanogenesis (also known as biomethanation) is the production of methane by microbes known as methanogens. The production of methane is an important and widespread form of microbial metabolism; and methanogenesis in microbes is a form of anaerobic respiration. Methanogenesis constitutes the final step in the decay of organic matter, during which electron acceptors (such as oxygen, ferric iron, sulfate, nitrate, and manganese) become depleted, while hydrogen ($H_2$) and carbon dioxide accumulate.

Generally, the hereinbelow-described methods of treating of subterranean formations are intended to increase the susceptibility of large carbonaceous molecules therein, such as comprise coal, to bioconversion into methane and other useful hydrocarbon products by indigenous and/or non-indigenous microbial consortia that are effective for such bioconversion—microbial consortia that comprise methanogens, or are methanogenic.

In one embodiment, the present invention relates to the treating of subterranean formations to increase the susceptibility (by way of chemical break down or solubilization, but not necessarily limited by these or any other theories) of large carbonaceous molecules therein, such as comprise coal, to bioconversion into methane and other useful hydrocarbon products by indigenous and/or non-indigenous microbial consortia, by introducing into the subterranean formations: (a) a solution containing at least one of an oxoacid ester of phosphorus or a thioacid ester of phosphorus; and (b) one or more other chemical compounds/chemical entities selected from the group consisting of: hydrogen, carboxylic acids, esters of carboxylic acids, salts of carboxylic acids, oxoacids of phosphorus, salts of oxoacids of phosphorus, vitamins, minerals, mineral salts, metals, and yeast extracts. The carboxylate compounds may be organic compounds having one or more carboxylate groups (e.g., COO" groups). These compounds are typically organic acids or their salts. Examples include salts of acetate (i.e., $H_3CCOO^-$); benzoate (i.e., Ph-COO$^-$, where Ph is a phenyl group); and formate (i.e., $HCOO^-$) among other carboxylate groups.

In one embodiment, the present invention relates to the treating of subterranean formations, such as comprise coal, to convert the coal into methane and other useful hydrocarbon products by indigenous and/or non-indigenous microbial consortia, by introducing into the subterranean formations: (a) a solution containing at least one of an oxoacid ester of phosphorus or a thioacid ester of phosphorus; (b) one or more other chemical compounds/chemical entities selected from the group consisting of: hydrogen, carboxylic acids, esters of carboxylic acids, salts of carboxylic acids, oxoacids of phosphorus, salts of oxoacids of phosphorus, vitamins, minerals, mineral salts, metals, and yeast extracts; and (c) a microbial consortia (preferably comprised of methanogens).

The hereinabove-noted and hereinbelow-noted "solution containing at least one of an oxoacid ester of phosphorus or a thioacid ester of phosphorus" may be produced in solution from the appropriate oxoacid or thioacid and the appropriate alcohol. Where referred to throughout this disclosure a "solution containing at least, one of an oxoacid ester of phosphorus or a thioacid ester of phosphorus" shall mean either "a solution containing at least one of an oxoacid ester of phosphorus or a thioacid ester of phosphorus" or a solution comprising the appropriate oxoacid or thioacid and the appropriate alcohol.

As used herein, coal refers to any of the series of carbonaceous fuels ranging from lignite to anthracite. The members of the series differ from each other in the relative amounts of moisture, volatile matter, and fixed carbon they contain. Of the coals, those containing the largest amounts of fixed carbon and the smallest amounts of moisture and volatile matter are the most useful to humans. The lowest in carbon content, lignite or brown coal, is followed in ascending order by sub-bituminous coal or black lignite (a slightly higher grade than lignite), bituminous coal, semibituminous (a high-grade bituminous coal), semianthracite (a low-grade anthracite), and anthracite.

For example, in a process for bioconverting coal by bacterial bioconversion, partially "etching" away the coal surfaces in coal bed cracks would expose relatively huge coal surface areas for bacteria to multiply, thereby considerably raising the volume of bioconversion per unit time.

Relatively deep coal mines can have temperatures near the boiling point of water. The treating system of the present invention for bioconversion of coal would be very compatible with such temperatures, since the treating agent can operate at elevated temperatures.

The coal may be lignite or any form or rank of coal, ranging from brown coal to anthracite.

The treating step is carried out at temperatures prevailing in the subterranean coal deposit In some embodiments the solution and/or other amendments may be preheated.

The treating step may be carried out at any pH, preferably in the range of 6 to 9. The treating step may be carried out at any pressure ranging from with a vacuum to greater than 5,000 psig.

The oxoacid ester of phosphorus may be an ester of phosphorous acid, phosphoric acid, hypophosphorous acid, polyphosphoric acid, or mixtures thereof.

The oxoacid of phosphorus may be phosphorous acid, phosphoric acid, hypophosphorous acid, polyphosphoric acid, or mixtures thereof.

Suitable alcohols include methanol, ethanol, ethylene glycol, propylene glycol, glycerol, pentaerythritol, trimethylol ethane, trimethylol propane, trimethylol alkane, alkanol, polyol, or mixtures thereof.

In a preferred embodiment the ester is a mono-acid and/or di-ester of an acid of phosphorous.

In producing the ester in situ from the acid and alcohol, the blend may have any ratio of the oxoacid of phosphorus to the alcohol. Preferably, the ratio of the oxoacid of phosphorus to the alcohol is from 10:1 to 1:10.

In producing the ester in situ from the acid and alcohol, the blend may have any ratio of the thioacid of phosphorus to the alcohol. Preferably, the ratio of the thioacid of phosphorus to the alcohol is from 10:1 to 1:10.

The method of the present invention can include regulating the water content of the blend before or during treating. Regulation of the water content can be carried out by removing water. Suitable techniques for doing so include molecular sieving, distillation, or adding a dehydrating agent to the blend.

The method of the present invention may also include sonicating the blend during or after the treating.

A further aspect of the present invention is directed toward treating the coal as part of a process for bioconverting coal. Suitable bioconversion includes formation of hydrocarbons such as methane, ethane, propane, and others, as well as carbon dioxide.

In one aspect coal may be bioconverted by an appropriate consortium of bacteria that includes for example, methanogens and acetogens. Such consortium may be inherently present in the coal deposit and/or may be added to the coal deposit. In addition, appropriate nutrients may be provided to the coal deposit to promote the growth of the bacteria present and/or added to the coal.

Thus, in accordance with an aspect of the invention, the treating agents used in the invention are injected into a coal bed as part of the overall procedure for bioconverting coal.

It is well known that hydrolysis equilibria are reversible for many chemicals. Phosphite esters are no exceptions (see Scheme 1 for an example). Thus, this process can proceed from left to right in each equilibrium step starting with P(OEt)$_3$ and water, or from right to left starting from phosphorous acid and ethanol at the lower right of the Scheme. Starting with 3 equivalents of EtOH and an equivalent of phosphorous acid and then removing the water (e.g., with molecular sieves) produces mainly P(OEt)$_3$.

Scheme 1

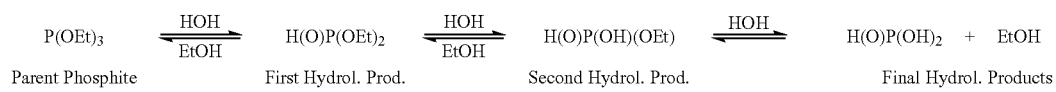

Parent Phosphite     First Hydrol. Prod.     Second Hydrol. Prod.     Final Hydrol. Products It is possible to start with phosphorous acid and the required alcohol to make a mixture of the first hydrolysis product and the second hydrolysis product for use as the active pretreatment medium or to start with the first hydrolysis product, and by adding the correct amount of water, make the same mixture as starting with phosphorous acid and the required alcohol.

It is generally possible to proceed in either direction of an equilibrium or sequence of equilibria. This process is governed by Le Chatelier's Principle.

The alcohols (see Table 1, below) from which A, (ethanol), B (ethylene glycol), C (propylene glycol), and D (2,2-dimethylpropylene-1,3-diol) are made are commercially inexpensive, are manufactured in large volumes, and are of very considerable industrial importance.

TABLE 1

| | |
|---|---|
| H(O)P(OEt)$_2$ | A |
|  | B |
| 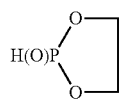 | C |
| 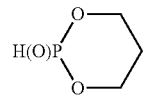 | D |

TABLE 1-continued

| | |
|---|---|
| 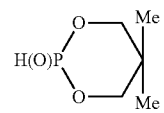 | D |
| EtOP(OEt)$_2$ | E |
|  | F |
| 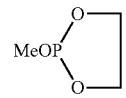 | G |
| 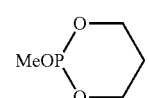 | H |
| H(O)POH(OEt) | I |

TABLE 1-continued

| | |
|---|---|
|  | J |
| 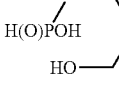 | K |
| 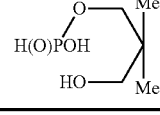 | L |

In Schemes 2, 3, and 4 (below), the polyols from which N, R, and V in these schemes are made are glycerol, trimethylol propane, and pentaerythritol, respectively (see Table 1, above). These polyols are very cheap and are made in large volumes (i.e., glycerol is an overly abundant byproduct of the biodiesel industry, trimethylol propane is used in polyurethane manufacture, and pentaerythritol is made in over 100 million pound quantities per year, most of which is used in alkyd resins and lubricants). Although the parent bicyclic phosphite M in Scheme 2 is known, it would not form in the proposed reaction of glycerol and phosphorous acid, because of its strained bonds and the fact that its formation would require the presence of a catalyst. A catalyst is also required for the analogous formations of the toxic parent phosphite Q in Scheme 3 and the non-toxic parent phosphite U shown in Scheme 4. It should be noted that neither first nor second hydrolysis products for the phosphite esters in Schemes 2-4 are commercially available, nor are there reports of their isolation to date.

thiophosphoric compounds are well known. However, such sulfur containing compounds could be more expensive and pose environmental problems.

Scheme 2

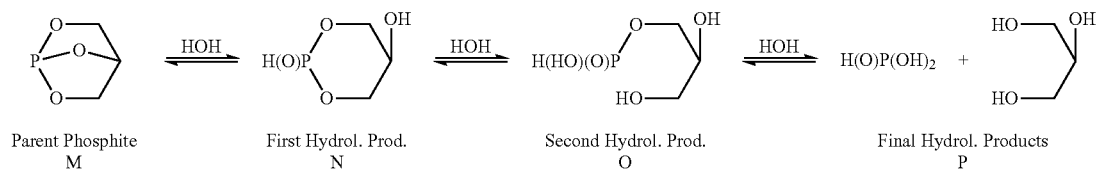

Scheme 3

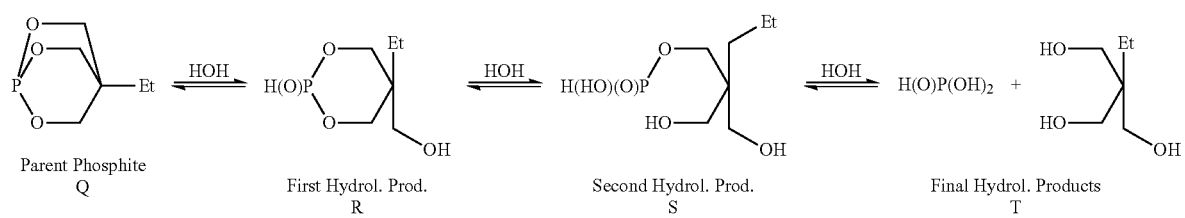

Scheme 4

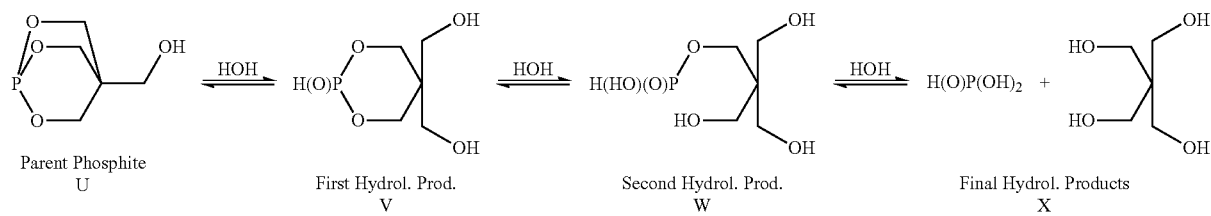

Synthesis of parent phosphite esters for subsequent hydrolysis (to make the desired ratio of first to second hydrolysis products) requires expense, time, and energy, which can be avoided by starting with phosphorous acid and the desired alcohol, diol, triol, or tetraol, followed by removing the appropriate amount of water. Note that the parent phosphite esters by themselves are ineffective agents. The mixture of active agents is created by proceeding from the final hydrolysis products and working toward parent phosphites but not actually synthesizing them.

The first hydrolysis products A-D of the parent phosphites E-H, respectively, are effective agents for coal. Compounds A, B, and D are commercially available, but C can be synthesized. It should be noted that A-D by themselves are also effective in the presence of some water to make a mixture of first and second hydrolysis products I-L.

One skilled in the art would recognize that thiophosphoryl compounds, those bearing the P=S functionality, may be substituted for related phosphoryl derivatives. Such substitution of a sulfur for one or more oxygens in a phosphorous oxoacid, an oxoacid ester, a phosphoric oxoacid, or a phosphoric acid ester would be possible as thiophosphorous and

In its broadest aspect the invention is directed to methods for the bioconversion of carbon-bearing materials in subterranean formations to methane and other useful hydrocarbons by treating the subterranean formation with a solution containing at least one of an oxoacid ester of phosphorus or a thioacid ester of phosphorus; and one or more other chemical compounds/chemical entities selected from the group consisting of: hydrogen, carboxylic acids, esters of carboxylic acids, salts of carboxylic acids, oxoacids of phosphorus, salts of oxoacids of phosphorus, vitamins, minerals, mineral salts, metals, and yeast extracts.

An ester of phosphite is a type of chemical compound with the general structure $P(OR)_3$. Phosphite esters can be considered as esters of phosphorous acid, $H_3PO_3$. A simple phosphite ester is trimethylphosphite, $P(OCH_3)_3$. Phosphate esters can be considered as esters of phosphoric acid. Since orthophosphoric acid has three —OH groups, it can esterify with one, two, or three alcohol molecules to form a mono-, di-, or triester. Without being bound by any particular theory or limits thereon, in the present invention, it is believed that the chemical compounds including esters of phosphite and phosphate, or an oxoacid ester of phosphorus, or a thioacid ester of phosphorus; or a mixture of an oxoacid of phosphorus and an alcohol, or a mixture of an thioacid of phosphorus and an alcohol; react with carbon-bearing molecules to break carbon bonds within the molecules and add hydrogen molecules to these carbon-bearing molecules, to thereby yield a range of smaller carbon-bearing molecules, such as carbon monoxide, carbon dioxide and volatile fatty acids, which are in turn more amenable to bioconversion by methanogenic microbial consortia to methane and other useful hydrocarbons. The reaction products produced from reaction of the introduced oxoacid ester of phosphorus or the thioacid ester of phosphorus; or the mixture of an oxoacid of phosphorus and an alcohol or the mixture of a thioacid of phosphorus and an alcohol; with coal may stimulate a methanogenic microbiological consortium in the subterranean formation to start producing, or increase production of, methane and other useful products.

Figure 1:
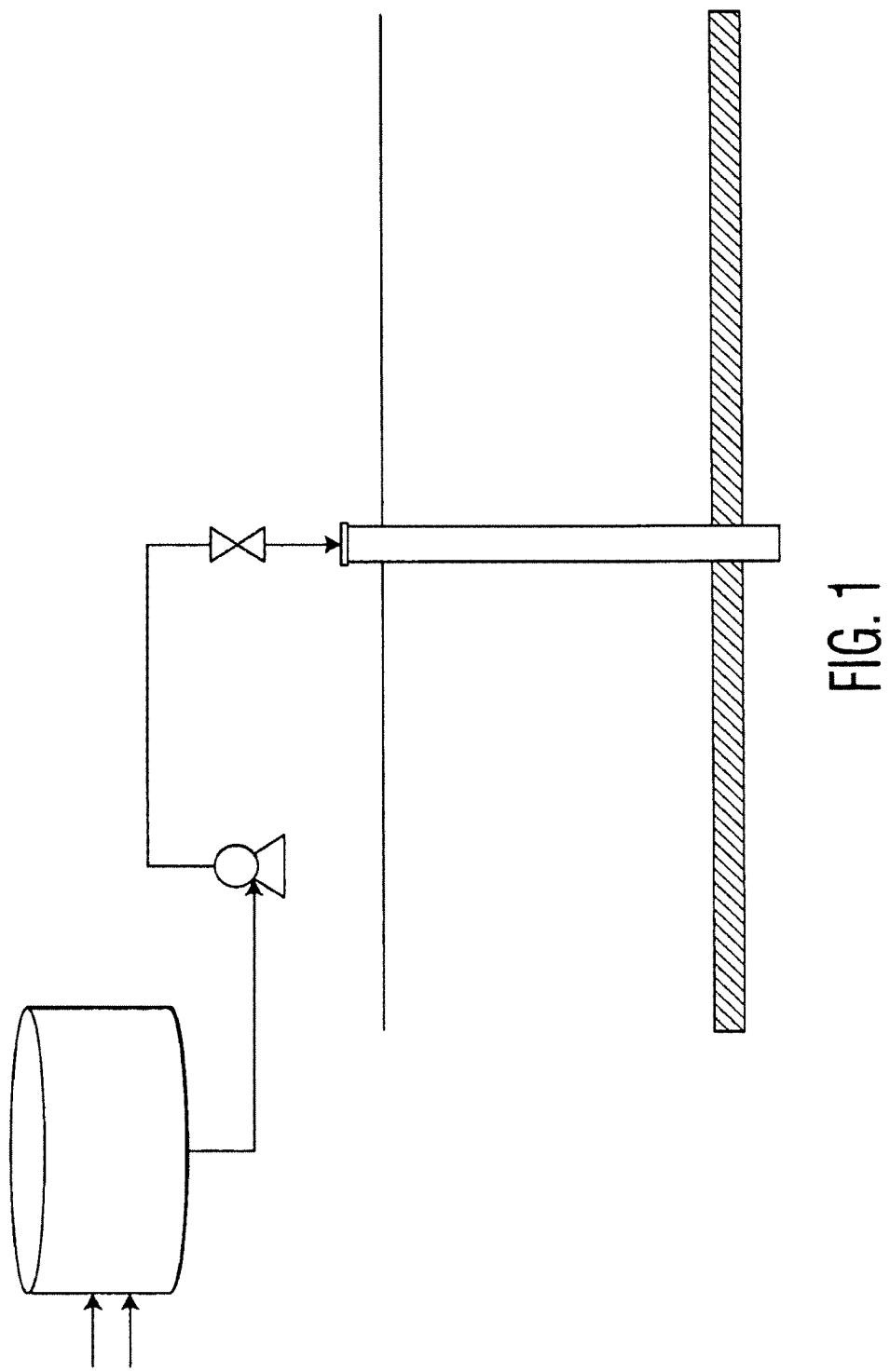
FIG. 1 illustrates a method of introducing a solution containing at least one of an oxoacid ester of phosphorus or a thioacid ester of phosphorus into a subterranean carbon-bearing formation according to the embodiments of the invention.

Referring to FIG. 1, a method of introducing a solution containing at least one of an oxoacid ester of phosphorus or a thioacid ester of phosphorus, into a subterranean carbon-bearing formation containing methanogenic microbial consortia is shown. The method includes accessing the subterranean formation. The subterranean formation may be a previously explored, carbon-bearing material deposit such as a coal mine, oil field, natural gas field, carbonaceous shale deposit, etc. Access to the subterranean formation containing methanogenic microbial consortia may involve utilizing previously mined or drilled access points to the formation. For access to unexplored formations, entries may be mined or drilled into, through various surface and subsurface formation layers.

Upon confirmation of access to the subterranean carbon-bearing formation containing methanogenic microbial consortia, a solution containing at least one of an oxoacid ester of phosphorus or a thioacid ester of phosphorus; and one or more other chemical compounds/chemical entities selected from the group consisting of: hydrogen, carboxylic acids, esters of carboxylic acids, salts of carboxylic acids, oxoacids of phosphorus, salts of oxoacids of phosphorus, vitamins, minerals, mineral salts, metals, and yeast extracts may be introduced into the formation. Providing the oxoacid ester of phosphorus or the thioacid ester of phosphorus; or the mixture of an oxoacid of phosphorus and an alcohol or the mixture of an thioacid of phosphorus and an alcohol; may involve the direct injection of these chemicals into the formation region containing the carbon-bearing materials and methanogenic microbial consortia. In addition, water and other chemicals may be added to the oxoacid ester of phosphorus or to the thioacid ester of phosphorus; or to the mixture of an oxoacid of phosphorus and an alcohol or to the mixture of an thioacid of phosphorus and an alcohol, either at the surface or at the point of introduction into the formation. These chemicals may undergo chemical and biochemical reactions en route to, or in, the formation that facilitates bioconversion. The reaction products may include a range of chemical compounds having a variety of forms, such as volatile fatty acids. These reaction products, such as volatile fatty acids, may be more readily metabolized by microorganisms in the formation to other chemicals, such as acetate and carbon dioxide, and then to methane and other useful hydrocarbon products.

Other chemicals such as hydrogen, carboxylic acids, esters of carboxylic acids, salts of carboxylic acids, oxoacids of phosphorus, salts of oxoacids of phosphorus, vitamins, minerals, mineral salts, metals, and yeast extracts may be introduced into the formation with the solution containing at least one of an oxoacid ester of phosphorus or a thioacid ester of phosphorus, alternately or in addition thereto. The additional phosphorous compounds may include phosphorous compounds such as $PO_x$, compounds where x is 2, 3, or 4 [e.g., such as sodium phosphate ($Na_3PO_4$) and potassium phosphate ($K_3PO_4$) as well as monobasic and dibasic derivatives of these salts (e.g., $KH_2PO_4$, $K_2HPO_4$, $NaH_2PO_4$, $Na_2HPO_4$, etc.)]. They may also include phosphorous oxyacids and/or salts of phosphorous oxyacids. For example, the phosphorous compounds may include $H_3PO_4$, $H_3PO_3$, and $H_3PO_2$ phosphorous oxyacids, as well as dibasic sodium phosphate and dibasic potassium phosphate salts. The phosphorous compounds may also include alkyl phosphate compounds (e.g., a trialkyl phosphate such as triethyl phosphate) and tripoly phosphates. The phosphorous compounds may further include condensed forms of phosphoric acid, including triphosphoric acid, pyrophosphoric acid, among others. They may also include the salts of condensed phosphoric acids, including alkali metals salts of tripolyphosphate (e.g., potassium or sodium tripolyphosphate), among other salts.

The solution containing at least one of an oxoacid ester of phosphorus or a thioacid ester of phosphorus; or a mixture of an oxoacid of phosphorus and an alcohol or a mixture of a thioacid of phosphorus and an alcohol, may be introduced into the formation along with hydrogen, either simultaneously or alternately, such that large molecules in the carbonaceous materials in the formation may be converted to compounds having a higher mol % of hydrogen atoms than the starting carbonaceous material, and/or a lower percentage of complex C—C bonds, that are thus more amenable to bioconversion to methane and other useful hydrocarbons.

The solution containing at least one of an oxoacid ester of phosphorus or a thioacid ester of phosphorus; or a mixture of an oxoacid of phosphorus and an alcohol or a mixture of a thioacid of phosphorus and an alcohol; may be introduced into the formation along with other amendments and nutrients, such as mineral salts and yeast extracts, either simultaneously or alternately, such that the growth and metabolic processes of methanogenic consortia may be enhanced as they bioconvert the carbonaceous materials in the formation. The yeast extracts may include digests and extracts of commercially available brewers and bakers yeasts.

Figure 2:
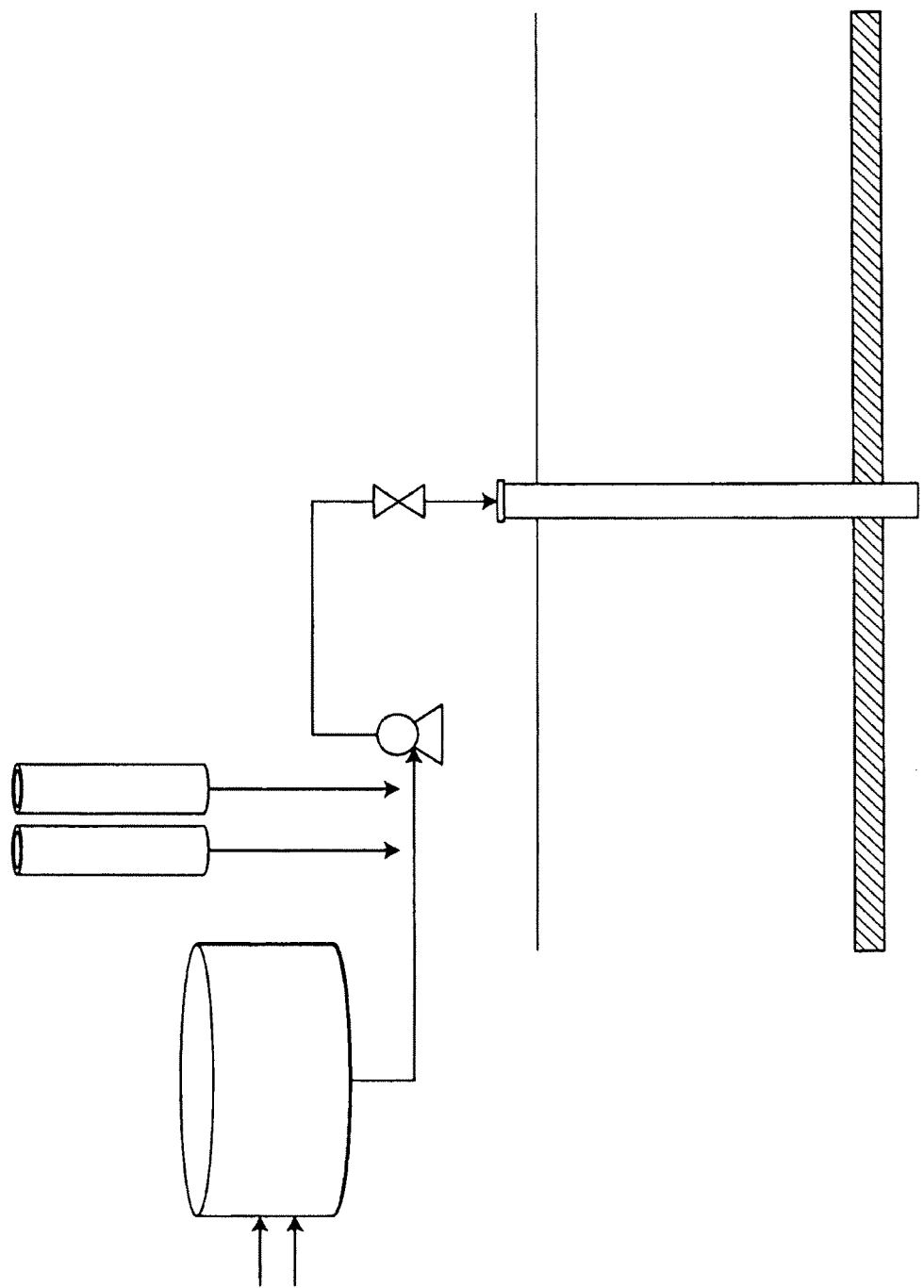
FIG. 2 illustrates a method of introducing (a) a solution containing at least one of an oxoacid ester of phosphorus or a thioacid ester of phosphorus; and (b) one or more other chemical compounds/chemical entities selected from the group consisting of: hydrogen, carboxylic acids, esters of carboxylic acids, salts of carboxylic acids, oxoacids of phosphorus, salts of oxoacids of phosphorus, vitamins, minerals, mineral salts, metals, and yeast extracts into a subterranean carbon-bearing formation according to embodiments of the invention.

FIG. 2 shows a method of introducing one or more chemical compounds/chemical entities selected from the group consisting of: hydrogen, carboxylic acids, esters of carboxylic acids, salts of carboxylic acids, oxoacids of phosphorus, salts of oxoacids of phosphorus, vitamins, minerals, mineral salts, metals, and yeast extracts into the formation with the solution containing at least one of an oxoacid ester of phosphorus or a thioacid ester of phosphorus; or with a mixture of an oxoacid of phosphorus and an alcohol or a mixture of a thioacid of phosphorus and an alcohol, alternately or in addition thereto, according to the embodiments of the invention. The method may include accessing the formation from the surface through a mine or a well(s) and delivering the chemicals, in situ. These other chemicals, vitamins and nutrients may enable the enhanced growth and improved metabolic processes of microorganisms that can metabolize the carbonaceous materials in the formation.

Figure 3:
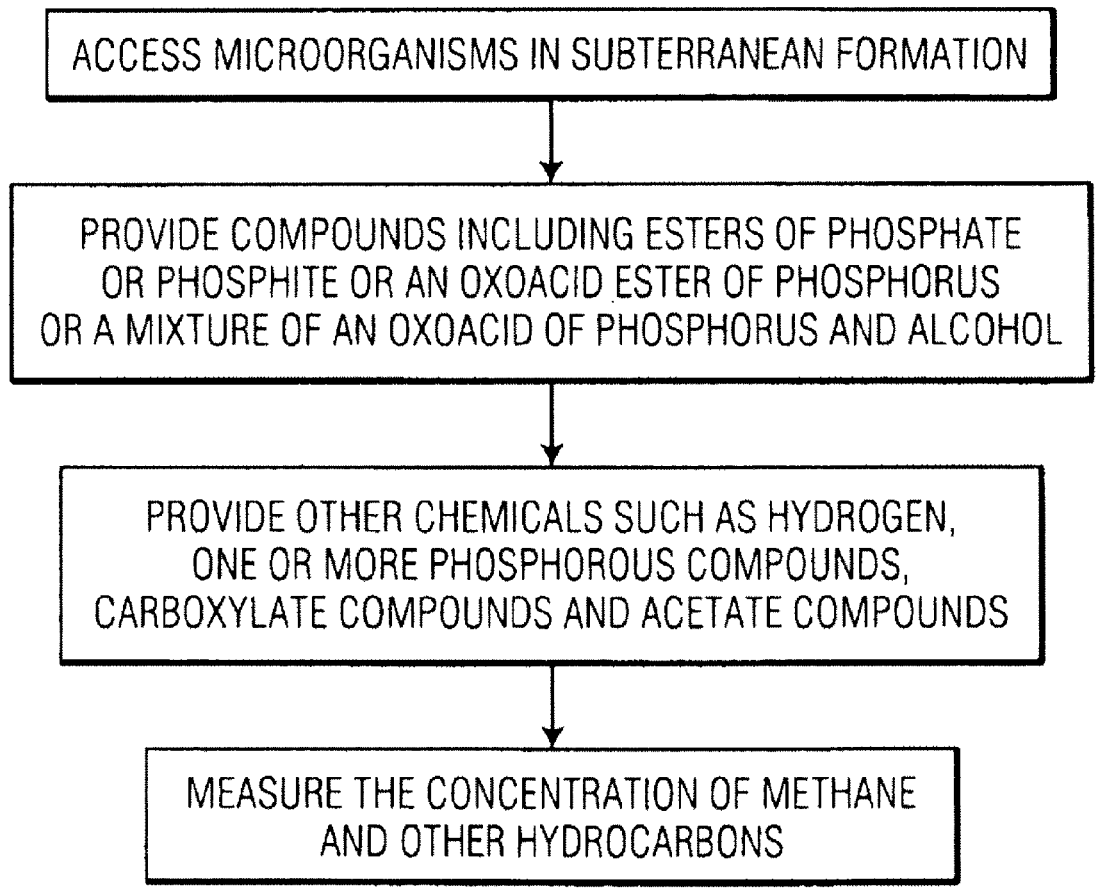
FIG. 3 is a flowchart illustrating a method of measuring the effects of introduced chemical compounds on the production of methane and other useful hydrocarbons from subterranean carbon-bearing formations according to embodiments of the invention.

The methods of the instant invention may also include measuring the concentration of the products that result from the treatment. For gas phase products, the partial pressure of the product in the formation may be measured, while aqueous products may involve measurements of molar concentrations. FIG. 3 shows the measurement of products being made after the introduction of the solution containing at least one of an oxoacid ester of phosphorus or a thioacid ester of phosphorus; or after the introduction of a mixture of an oxoacid of phosphorus and an alcohol or a mixture of a thioacid of phosphorus and an alcohol. Measurements may also be made before introducing the solution containing at least one of an oxoacid ester of phosphorus or a thioacid ester of phosphorus; or before introducing a mixture of an oxoacid of phosphorus and an alcohol or a mixture of a thioacid of phosphorus and an alcohol; and thereby enable a comparison of the resulting product concentrations.

The methods of the instant invention may also include measuring the concentration of a metabolic product. For gas phase metabolic products, the partial pressure of the product in the formation may be measured, while aqueous metabolic products may involve measurements of molar concentrations. FIG. 3 shows the measurement of metabolic products being made after the introduction of an oxoacid ester of phosphorus or a mixture of the solution containing at least one of an oxoacid ester of phosphorus or a thioacid ester of phosphorus; or after the introduction of a mixture of an oxoacid of phosphorus and an alcohol or a mixture of a thioacid of phosphorus and an alcohol. Measurements may also be made before introducing the solution containing at least one of an oxoacid ester of phosphorus or a thioacid ester of phosphorus; or before introducing a mixture of an oxoacid of phosphorus and an alcohol or a mixture of a thioacid of phosphorus and an alcohol; and thereby enable a comparison of the resulting metabolic product concentrations.

Referring now to FIG. 3, a flowchart illustrating a method of measuring the effects of introduced amendments on the production of metabolic products from geologic formations is shown. The method includes accessing the microorganisms in a carbonaceous material-containing geologic formation. The method also includes providing an amendment to the microorganisms in the formation, with the amendment comprising a solution containing at least one of an oxoacid ester of phosphorus or a thioacid ester of phosphorus; or a mixture of an oxoacid of phosphorus and an alcohol or a mixture of a thioacid of phosphorus and an alcohol. Embodiments of the present invention also include providing amendments in addition to the solution containing at least one of an oxoacid ester of phosphorus or a thioacid ester of phosphorus; or in addition to a mixture of an oxoacid of phosphorus and an alcohol or a mixture of a thioacid of phosphorus and an alcohol; such as hydrogen, carboxylic acids, esters of carboxylic acids, salts of carboxylic acids, oxoacids of phosphorus, salts of oxoacids of phosphorus, vitamins, minerals, mineral salts, metals, and yeast extracts. The amendments may still further include water amendments to dilute metabolic inhibitors and/or the microorganism consortium. The effect of the amendments can be analyzed by measuring the concentration of a metabolic intermediary, or the concentration of the metabolic product such as methane in the formation environment.

If the product concentration and/or rate of product generation does not appear to be reaching a desired level, adjustments may be made to the composition of the amendment.

In another embodiment of the invention, an initial analysis of the microorganism formation environment may be conducted before the amendment is introduced. This analysis may include measuring the chemical composition that exists in the environment. This may include an in situ analysis of the chemical environment by methods that are known to those skilled in the art, and/or extracting gases, liquids, and solid substrates from the formation for a remote analysis by other methods that are known to those skilled in the art.

For example, extracted formation samples may be analyzed using spectrophotometry, NMR, HPLC, gas chromatography, mass spectrometry, voltammetry, and other chemical instrumentation. The tests may be used to determine the presence and relative concentrations of elements like dissolved carbon, phosphorous, nitrogen, sulfur, magnesium, manganese, iron, calcium, zinc, tungsten, cobalt and molybdenum, among other elements. The analysis may also be used to measure quantities of polyatomic ions such as $PO_2^{3-}$, $PO_3^{3-}$, and $PO_4^{3-}$, $NH_4^+$, $NO_2^-$, $NO_3^-$, and $SO_4^{2-}$, among other ions. The quantities of vitamins, and other nutrients may also be determined. An analysis of the pH, salinity, oxidation potential (Eh), and other chemical characteristics of the formation environment may also be performed. Microorganism activity analyses may also be performed on extracted consortium samples. These analyses may include the use of $^{14}C$-acetate, $^{14}C$-bicarbonate, and other methanogen substrates to estimate methanogenic activity in samples including formation water collected before and during field applications. Additional details of analyses that may be performed are described in PCT Application No. PCT/US2005/015259, filed May 3, 2005; and U.S. patent application Ser. No. 11/343,429, filed Jan. 30, 2006, the disclosures of each of which are hereby incorporated by reference in their entireties.

As a component part of the hereinabove described and hereinbelow described methods, a biological analysis of the microorganisms may also be conducted, in accordance with procedures that are known to those skilled in the art. This may include a quantitative analysis of the population size determined by direct cell counting techniques, including the use of microscopy, flow cytometry, plate counts, as well as indirect techniques, such as DNA quantification, phospholipid fatty acid analysis, quantitative PCR, protein analysis, etc. The identification of the genera and/or species of one or more members of the microorganism consortium by genetic analysis may also be conducted. For example, an analysis of the DNA of the microorganisms may be done where the DNA is optionally cloned into a vector and suitable host cell to amplify the amount of DNA to facilitate detection. In some embodiments, the detecting may be of all or part of ribosomal DNA (rDNA), of one or more microorganisms. Alternatively, all or part of another DNA sequence unique to a microorganism may be detected. Detection may be by use of any appropriate means known to the skilled person. Non-limiting examples include restriction fragment length polymorphism (RFLP) or terminal restriction fragment length polymorphism (TRFLP); polymerase chain reaction (PCR); DNA-DNA hybridization, such as with a probe, Southern analysis, or the use of an array, microchip, bead based array, or the like; denaturing gradient gel electrophoresis (DGGE); or DNA sequencing, including sequencing of cDNA prepared from RNA as non-limiting examples. Additional details of the biological analysis of the microorganisms are described in U.S.

patent application Ser. No. 11/099,879, filed Apr. 5, 2005, the disclosures of which are hereby incorporated by reference in their entireties.

The method may also include removing the metabolic product such as methane from the formation. Removal may be triggered when the concentration of the reaction product increases above a threshold level in the formation. In some of these instances, removal may be performed to keep the product in a concentration range that has been found to stimulate the microorganisms to generate more of the product.

What is claimed is:

1. A method of treating a subterranean formation to convert coal therein to methane, said method comprising the steps of:
    (a) introducing into said subterranean formation a solution containing at least one of an oxoacid ester of phosphorus or a thioacid ester of phosphorus; and
    (b) introducing into said subterranean formation one or more other chemical compounds/chemical entities selected from the group consisting of: hydrogen, carboxylic acids, esters of carboxylic acids, salts of carboxylic acids, oxoacids of phosphorus, salts of oxoacids of phosphorus, vitamins, minerals, mineral salts, metals, and yeast extracts.

2. The method of claim 1, wherein said introduction into said subterranean formation of said solution of step (a) is by direct injection into said subterranean formation.

3. The method of claim 1, wherein water and/or other chemicals are added to said solution of step (a) either at the surface or at the point of introduction into said subterranean formation.

4. The method of claim 1, whereby the steps (a) and (b) are performed simultaneously.

5. The method of claim 1, whereby the steps (a) and (b) are performed at different times.

6. A method of treating a subterranean formation to convert coal therein to methane, said method comprising the steps of:
    (a) introducing into said subterranean formation a solution containing at least one of an oxoacid ester of phosphorus or a thioacid ester of phosphorus;
    (b) introducing into said subterranean formation one or more other chemical compounds/chemical entities selected from the group consisting of: hydrogen, carboxylic acids, esters of carboxylic acids, salts of carboxylic acids, oxoacids of phosphorus, salts of oxoacids of phosphorus, vitamins, minerals, mineral salts, metals, and yeast extracts; and (c) a microbial consortia (preferably comprised of methanogens).

7. The method of claim 6, wherein said microbial consortia are indigenous to said subterranean formation.

8. The method of claim 6, wherein said microbial consortia are non-indigenous to said subterranean formation.

9. The method of claim 6, wherein said microbial consortia comprise of both microbes that are indigenous to said subterranean formation and microbes that are non-indigenous to said subterranean formation.

10. The method of claim 6, wherein said introduction into said subterranean formation of said solution of step (a) is by direct injection into said subterranean formation.

11. The method of claim 6, wherein water and/or other chemicals are added to said solution of step (a) either at the surface or at the point of introduction into said subterranean formation.

12. The method of claim 6, whereby the steps (a) and (b) are performed simultaneously.

13. The method of claim 6, whereby the steps (a) and (b) are performed at different times.

* * * * *